United States Patent [19]

Rivadeneira et al.

[11] Patent Number: 5,502,194

[45] Date of Patent: Mar. 26, 1996

[54] PROCESS FOR THE PREPARATION OF 2-HALOGENO-PYRIDINE DERIVATIVES

[75] Inventors: Eric Rivadeneira, Leverkusen; Klaus Jelich, Wuppertal, both of Germany

[73] Assignee: Bayer Aktiengesellschaft, Leverkusen, Germany

[21] Appl. No.: 220,620

[22] Filed: Mar. 31, 1994

Related U.S. Application Data

[63] Continuation-in-part of Ser. No. 205,121, Feb. 28, 1994, which is a continuation-in-part of Ser. No. 15,715, Feb. 9, 1993, abandoned.

[30] Foreign Application Priority Data

Feb. 19, 1992 [DE] Germany ............... 42 04 920.2
Apr. 15, 1992 [DE] Germany ............... 42 12 595.2
Apr. 6, 1993 [DE] Germany ............... 43 11 247.1

[51] Int. Cl.⁶ .......... C07D 213/22; C07D 213/56; C07D 213/73; C07D 213/80
[52] U.S. Cl. .......... 546/257; 546/286; 546/304; 546/316; 546/318; 546/345
[58] Field of Search .................... 546/257, 304, 546/286, 316, 318

[56] References Cited

FOREIGN PATENT DOCUMENTS

| | | | |
|---|---|---|---|
| 0438691 | 7/1991 | European Pat. Off. | 546/286 |
| 0439745 | 8/1991 | European Pat. Off. | 546/345 |
| 0463464 | 1/1992 | European Pat. Off. | 546/345 |
| 0556683 | 8/1993 | European Pat. Off. | 546/345 |

OTHER PUBLICATIONS

Chemical Abstracts, 27–Hetrocycles, vol. 120, 1994, p. 8480; CA# 8476b: "Process for the preparation of 2–chloro–5–methyl . . . ", E. Rivadeneira et al.
Phys. Org., J. Chem. Soc. (B), 1971, pp. 1675–1682; "Kinetics of Reactions in Heterocycles. Part VIII . . . ", G. B. Barlin et al.
Chemical Abstracts, vol. 85, 1976, p. 538; CA# 40429h: "Studies on the quantitative determination of pyridine . . . ", R. Zalewski et al.
J. C. S. Chem. Comm., 1974, pp. 500–501; "The Dimer of 1–(5–Nitro–2–pyridyl)–3–oxidopyridinium and its Reactions", N. Dennis et al.
Chemical Abstracts, 51–Fossil Fuels, vol. 87, 1977, p. 127; CA# 41587m: "Studies on the quantitative determination of . . . ", R. Zalewski et al.
Chemical Abstracts, 79–Inorganic Anal. Chem., vol. 107, 1987, p. 877; CA# 211056p: "Synthesis of the new color reagent . . . ", G. Yang et al.

Chemical Abstracts, 26–Biomolecules, vol. 112, 1990, p. 489; CA# 20851n: "Cephalosporin derivatives", R. H. Bradbury et al.
J. C. S. Perkin I, pp. 1436–1977; "Syntheis, Spectroscopic Properties, and Chemistry of . . . ", A. Sultan Afridi et al.
J. Chem. Soc. Perkin Trans. I–1983, pp. 2623–2627; "Nucleophilic Displacement of N–Aryl and Heteroaryl Groups . . . ", A. R. Katritzky et al.
Chemical Abstracts, vol. 89, 1978, p. 574; CA# 215188r: "Preparation of some novel pyridone derivatives", A. R. Katritzky.
Barlin et al., Journal of The Chem. Society, (B) pp. 1675–1681 (1971).

*Primary Examiner*—Alan L. Rotman
*Attorney, Agent, or Firm*—Sprung Horn Kramer & Woods

[57] ABSTRACT

A process for the preparation of a 2-halogeno-pyridine of the formula

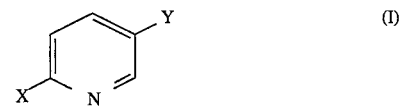

(I)

in which
 X represents halogen and
 Y represents halogen, nitro, formyl, cyano, carboxyl, carbamoyl, alkyl, halogenoalkyl, alkoxyalkyl, dialkoxyalkyl, alkoxycarbonyl, alkylaminocarbonyl or dialkylaminocarbonyl, which comprises in a first stage reacting a pyridine 1-oxide of the formula

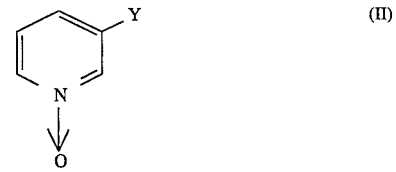

(II)

with an organic nitrogen base A and an electrophilic compound, optionally in the presence of a diluent, to produce a compound of the formula

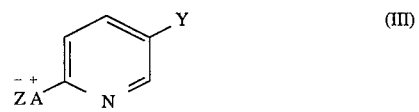

(III)

in which
 A represents the radical of an organic nitrogen base, and
 Z⁻ represents an anion formed from an electrophilic compound, optionally isolating and optionally purifying the compound of the formula (III).

4 Claims, No Drawings

PROCESS FOR THE PREPARATION OF 2-HALOGENO-PYRIDINE DERIVATIVES

This application is a continuation-in-part of application Ser. No. 08/205,121, filed Feb. 28, 1994, now pending, which is a continuation-in-part of application Ser. No. 08/015,715, filed Feb. 9, 1993, now abandoned.

The invention relates to a new process for the preparation of 2-halogeno-pyridine derivatives and to new intermediate products for this process.

It is known that 2-halogeno-pyridine derivatives are obtained when corresponding pyridine 1-oxides are reacted with phosphoryl chloride (compare Chem. Pharm. Bull. 36 (1988), 2244–2247; and EP-A 324174/LeA 25745), with chlorine-containing phosphoric acid derivatives (compare EP-A 370317/LeA 26429), with carboxylic acid chlorides (compare EP-A 438691/LeA 27429), with sulphonic acid chlorides, (compare EP-A 463464/LeA 27658, or with other chlorinating agents (compare EP-A 439745/LeA 27472), if appropriate in the presence of basic organic nitrogen compounds.

However, the yields achieved in these processes and the quality of the products thereby obtained, which often contain considerable amounts of isomers, are not satisfactory in many cases.

A process for the preparation of 2-chloro-5-methylpyridine in which 3-methyl-pyridine 1-oxide is first reacted with an organic nitrogen base to give a 1:1 adduct which can be isolated, and the latter is reacted with a chlorinating agent is the subject-matter of a prior patent application which has not been previously published (compare DE-P 4204920/LeA 28939).

It has now been found that 2-halogeno-pyridine derivatives of the general formula (I)

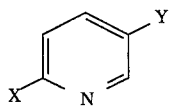

in which

X represents halogen and

Y represents halogen, nitro, formyl, cyano, carboxyl, carbamoyl, alkyl, halogenoalkyl, alkoxyalkyl, dialkoxyalkyl, alkoxycarbonyl, alkylaminocarbonyl or dialkylaminocarbonyl, can be obtained in good yields and in good quality if in a first stage, pyridine 1-oxides of the general formula (II)

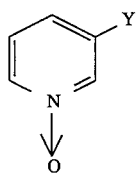

in which

Y has the abovementioned meaning, are reacted with an organic nitrogen base A and an electrophilic compound, if appropriate in the presence of a diluent, to give compounds of the general formula (III)

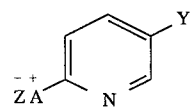

in which

A represents the radical of an organic nitrogen base,

Y has the abovementioned meaning and $Z^-$ represents an anion formed from an electrophilic compound, the compounds of the formula (III) are isolated as crude products, if appropriate, or if appropriate further purified, and in a second stage, these compounds are reacted with a halogenating agent, if appropriate in the presence of an alkyl halide and if appropriate in the presence of a diluent, at temperatures between 10° C. and 150° C.

Surprisingly, 2-halogeno-pyridine derivatives of the formula (I) can be obtained in high yields and in a considerably improved isomer purity (in comparison with the known procedure) by the process according to the invention. Unreacted intermediate products of the formula (III) can be employed again in the process.

The process according to the invention is thus a valuable enrichment of the prior art.

The process according to the invention preferably relates to the preparation of compounds of the formula (I) in which X represents fluorine, chlorine, bromine or iodine and represents fluorine, chlorine, bromine, iodine, nitro, formyl, cyano, carboxyl or carbamoyl, or represents $C_1$–$C_4$-alkyl which is optionally substituted by fluorine, chlorine or bromine (mono- to trisubstituted) or by $C_1$–$C_4$-alkoxy (mono- or dissubstitutued), or represents $C_1$–$C_4$-alkoxy-carbonyl, $C_1$–$C_4$-alkylamino-carbonyl or di-($C_1$–$C_4$-alkyl)-aminocarbonyl.

The process according to the invention particularly relates to the preparation of compounds of the formula (I) in which X represents fluorine, chlorine or bromine and represents fluorine, chlorine, bromine, formyl, cyano, carboxyl, carbamoyl, ethyl, n- or i-propyl, n-, i-, s- or t-butyl, trifluoromethyl, trichloromethyl, tribromomethyl, difluoromethyl, dichloromethyl, dibromomethyl, fluoromethyl, chloromethyl, bromomethyl, methoxymethyl, ethoxymethyl, n- or i-propoxymethyl, n-, i-, s- or t-butoxymethyl, dimethoxymethyl or diethoxymethyl, methoxycarbonyl, ethoxycarbonyl, methylaminocarbonyl, ethylaminocarbonyl, dimethylaminocarbonyl or diethylaminocarbonyl.

If, for example, 3-fluoro-pyridine 1-oxide is used as the starting substance, trimethylamine is used as the organic nitrogen base A and phosgene is used as the electrophilic compound in the first process stage and phosgene is used as the halogenating agent in the second process stage, the course of the reaction in the process according to the invention can be outlined by the following equation:

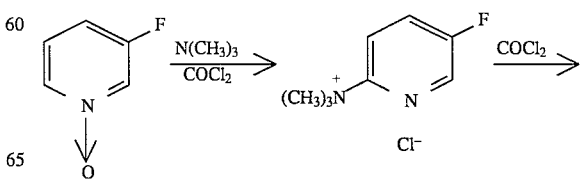

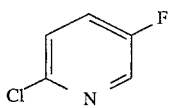

If trimethylamine is used as the organic nitrogenous base A and phosgene is used as the electrophilic compound in the first stage and as the chlorinating agent in the second stage, the reaction course for the process according to the invention may be outlined for example by the following scheme:

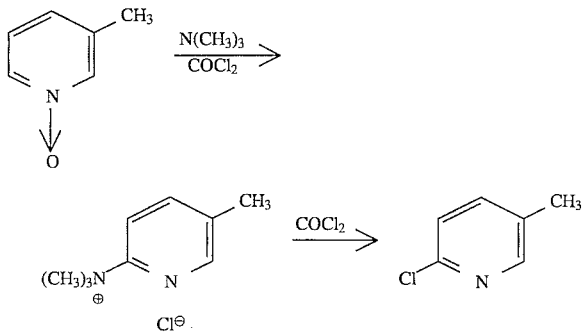

Formula (II) provides a general definition of the pyridine 1-oxides to be used as starting substances in the process according to the invention for the preparation of compounds of the formula (I).

In formula (II) Y preferably or in particular has that meaning which has already been mentioned above as preferred or as particularly preferred in connection with the description of the compounds of the formula (I) to be prepared according to the invention.

The starting substances of the formula (II) are known organic chemicals (compare J. Chem. Soc. 1959, 3680–3683, J. Med. Chem. 11 (1968), 1172–1176; Liebigs Ann. Chem. 618 (1958), 152–158, Z. Chem 10 (1970), 184–185) and JACS 76 (1954), 1286–1291).

Formula (III) provides a general definition of the adducts formed in the first stage of the process according to the invention.

Preferably, in formula (III),

A represents an organic nitrogen base from the series comprising tri-($C_1$–$C_4$-alkyl)-amine, N,N-di-($C_1$–$C_4$-alkyl)-benzylamine, N,N-di-($C_1$–$C_4$-alkyl)-cyclohexylamine or represents pyridine, which is optionally mono- to trisubstituted by $C_1$–$C_4$-alkyl and $Z^-$ represents a chloride ion or a $C_1$–$C_4$-alkyl-carboxylate ion; and Y preferably has that meaning which has been mentioned above as preferred in connection with the description of the compounds of the formula (I) to be prepared according to the invention.

In particular, in formula (III),

A represents trimethylamine, triethylamine, tripropylamine, tributylamine, N,N-dimethyl-benzylamine, N-N-diethylbenzylamine, N,N-dimethyl-cyclohexylamine, N,N-diethyl-cyclohexylamine or pyridine, which is optionally mono- or disubstituted by methyl or ethyl, and $Z^-$ represents a chloride ion or an acetate ion; and Y in particular has that meaning which has been mentioned above as particularly preferred in connection with the description of the compounds of the formula (I) to be prepared according to the invention.

The adducts of the formula (III) are not yet known from the literature and are, as new chemical compounds, the subject-matter of the present patent application.

The process according to the invention is carried out using an organic nitrogen base A in the first stage. The preferred or particularly preferred meaning of A can be seen from the definition of the compounds of the formula (III).

Trimethylamine is very especially preferred as the organic nitrogen base for the process according to the invention.

An electrophilic compound furthermore is employed in the first stage of the process according to the invention. Preferred electrophilic compounds for the process according to the invention are acid chlorides and anhydrides, for example acetyl chloride, propionyl chloride, acetic anhydride, propionic anhydride, benzoyl chloride, benzotrichloride, phosgene, oxalyl chloride, benzenesulphonyl chloride, p-toluenesulphonyl chloride, phosphorus(III) chloride, phosphoryl chloride (phosphorus oxychloride), phosphorus(V) chloride, thionyl chloride, sulphuryl chloride, dichloromethylene-dimethylimmonium chloride, cyanuric chloride and chlorotrimethylsilane.

Phosgene, thionyl chloride, sulphuryl chloride, benzenesulphonyl chloride and p-toluenesulphonyl chloride are particularly preferred electrophilic substances employed for the process according to the invention.

The process according to the invention is carried out using a halogenating agent in the second stage. Preferred halogenating agents in the process according to the invention are compounds which can donate halogen ions to other reaction partners, for example acetyl chloride, benzoyl chloride, phosgene, oxalyl chloride, benzenesulphonyl chloride, phosphorus(III) chloride, phosphorus(III) bromide, phosphoryl chloride, phosphorus(V) chloride, thionyl chloride, sulphuryl chloride, hydrogen chloride, hydrogen fluoride, hydrogen bromide, tetraethylammonium chloride, tetrabutylammonium chloride and benzyl-triethylammonium chloride.

Phosgene, hydrogen fluoride, hydrogen chloride and hydrogen bromide are particularly preferred halogenating agents in the second stage of the process according to the invention.

The process according to the invention is carried out in the presence of an alkyl halide, if appropriate, in the second stage. Preferred alkyl chlorides are methyl chloride, methyl bromide, ethyl chloride, propyl chloride and butyl chloride, in particular methyl chloride.

In the first stage, the process according to the invention is preferably carried out using a diluent. Possible diluents are practically all inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone and methyl ethyl, methyl isopropyl and methyl isobutyl ketone, esters, such as methyl and ethyl acetate, nitriles, such as, for example, acetonitrile and propionitrile, amides, such as, for example, dimethylformamide, dimethylacetamide and N-methylpyrrolidone, and dimethyl sulphoxide, tetramethylene sulphone and hexamethylphosphoric acid triamide.

If appropriate, the process according to the invention is also carried out in the presence of a diluent in the second stage. Possible diluents here are, in addition to water, practically all inert organic solvents. These include, preferably, alcohols, such as methanol, ethanol and n- and i-propanol, carboxylic acids, such as formic acid, acetic acid and propionic acid, and the solvents mentioned above for the first stage of the process according to the invention.

If trimethylamine is employed as the organic nitrogen base, the first stage of the process according to the invention is in general carried out in the temperature range between −50° C. and +120° C., preferably between −30° C. and +80° C. If organic nitrogen bases other than trimethylamine are employed, the first stage is in general carried out in the temperature range from −30° C. to +100° C., preferably between −15° C. and +10° C.

The first stage of the process according to the invention is in general carried out under normal pressure. However, it is also possible to carry out the first stage under increased or reduced pressure, in general between 0.1 and 100 bar.

For carrying out the first stage of the process according to the invention, in general between 1 and 10 mol, preferably between 1 and 5 mol, of organic nitrogen base and between 1 and 10 mol, preferably between 1 and 5 mol, of electrophilic compound are employed per mole of starting compound of the formula (II).

In a preferred embodiment of the first stage of the process according to the invention, the starting compound of the formula (II) is initially introduced into a diluent and, after cooling, first the organic nitrogen base and then the electrophilic compound are slowly metered in successively, while stirring.

After the end of the reaction, the more volatile components are distilled off under reduced pressure, if appropriate. The crude intermediate product, which essentially contains the adduct of the formula (III), can be purified in the customary manner, for example by column chromatography, or also employed in the second stage in the crude state.

Preferably, the crude intermediate product as such—if appropriate also without removal of the diluent—is employed in the second stage.

The second stage of the process according to the invention is in general carried out in the temperature range between 10° C. and 150° C., preferably between 20° C. and 120° C., in particular between 30° C. and 110° C.

The second stage of the process according to the invention is in general carried out under normal pressure. However, it is also possible to carry out the second stage under increased or reduced pressure, in general between 0.01 and 200 bar.

Working up can be carried out in the customary manner. For example, the crude product is digested with an organic solvent which is practically immiscible with water, washed with water and dried. After careful removal of the organic solvent by distillation under reduced pressure, a residue which essentially contains the product of the formula (I) remains.

The 2-halogeno-pyridine derivatives which can be prepared by the process according to the invention can be employed as intermediate products for the preparation of pharmaceuticals (compare DE-A 2812585) or of plant treatment agents (compare DE-A 2630046, EP-A 192060, DE-A 3726993 and DE-A 3924682).

Preparation Examples

EXAMPLE 1

1st Stage:

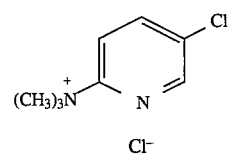

47.2 g (0.8 mol) of trimethylamine are condensed into a solution of 32.4 g (0.25 mol) of 3-chloropyridine N-oxide in 250 ml of 1,2-dichloroethane at −25° C. 52.95 g (0.31 mol) of benzenesulphonyl chloride are added dropwise at 0° C. in the course of 40 minutes. The mixture is stirred at 0° C. for 2 hours and then allowed to thaw overnight. It is concentrated in vacuo at a bath temperature of below 50° C. and the residue is purified by repeated column chromatography.

24.3 g (47% of theory) of trimethyl-2-(5-chloropyridyl)ammonium chloride are obtained.

$^1$H-NMR (300 MHz, $D_6$-DMSO: δ/ppm=3.63 (9H, singlet), 8.25 (IH, doublet, J=8.7 Hz), 8.42 (IH, doublet of doublet, $J_1$=9 Hz, $J_2$=2.4 Hz, 8.77 (IH, doublet, J=2.4 Hz).

2nd stage:

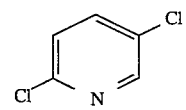

Trimethyl-2-(5-chloropyridyl)-ammonium chloride is prepared in accordance with the above specification starting from 32.4 g (0.25 mol) of 3-chloropyridine N-oxide, but without purification of the crude product by column chromatography. The crude product is introduced into 500 ml of 1,2-dichloroethane, and gaseous hydrogen chloride is added at 50° C. for 30 hours. The mixture is then concentrated, the residue is taken up in water and the mixture is brought to pH 9–10 with dilute sodium hydroxide solution and extracted three times with methylene chloride. The combined organic phases are dried over sodium sulphate, filtered and concentrated on a rotary evaporator. The crude product is then purified by column chromatography.

19.7 g (53% of theory, based on the 3-chloropyridine N-oxide employed) of 2,5-dichloropyridine are obtained.

EXAMPLE 2

1st Stage:

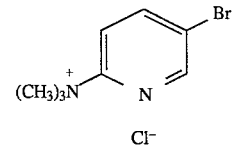

41.9 g (0.71 mol) of trimethylamine are condensed into a solution of 37.4 g (0.215 mol) of 3-bromopyridine N-oxide in 250 ml of 1,2-dichloroethane at −25° C. 45.6 g (0.258 mol) of benzenesulphonyl chloride are added dropwise at 0° C. in the course of 1 hour. The mixture is subsequently stirred at 0° C. for 2 hours and is allowed to thaw overnight. It is concentrated in vacuo at a bath temperature of below 50° C. and the residue is purified by several column chromatography operations.

27.4 g (50.7% of theory) of trimethyl-2-(5-bromopyridyl)-ammonium chloride are obtained.

$^1$H-NMR (300 MHz, $D_6$-DMSO): δ/ppm=3.61 (9H, singlet), 8.145 (IH, doublet, J=8.7 Hz), 8.54 (IH, doublet of doublet, $J_1$=9 Hz, $J_2$=2.4 Hz), 8.85 (IH, doublet, J=2.4 Hz).

2nd Stage:

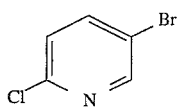

Trimethyl-2-(5-bromopyridyl)-ammonium chloride is prepared in accordance with the above specification starting from 52.2 g (0.3 mol) of 3-bromopyridine N-oxide, but without purification of the crude product by column chromatography. The crude product is introduced into 500 ml of 1,2-dichloroethane, and gaseous hydrogen chloride is added at 50° C. for 30 hours. The mixture is then concentrated, the residue is taken up in water and the mixture is rendered alkaline with dilute sodium hydroxide solution (pH 9–10) and extracted three times with methylene chloride. The combined organic phases are dried over sodium sulphate, filtered and concentrated on a rotary evaporator. The crude product is purified by column chromatography.

32.7 g (56.6% of theory) based on the 3-bromopyridine N-oxide employed) of 5-bromo-2-chloropyridine are obtained.

EXAMPLE 3

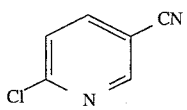

6 g (0.03 mol) of trimethyl-2-(5-cyanopyridyl)-ammonium chloride are introduced into 80 ml of 1,2-dichloroethane, and gaseous hydrogen chloride is added at 50° C. for 5 hours. The mixture is then concentrated, the residue is taken up in water and the mixture is brought to pH 9–10 with sodium hydroxide solution and extracted three times with methylene chloride. The combined organic phases are dried over sodium sulphate, filtered and concentrated on a rotary evaporator.

3.8 g (91% of theory) of 2-chloro-5-cyanopyridine are obtained.

EXAMPLE 4

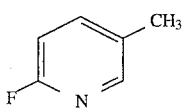

54.5 g (0.5 mol) of 3-methylpyridine 1-oxide are initially introduced into 350 ml of methylene chloride and the mixture is cooled to 0° C. 202 g (2 mol) of trimethylamine are condensed into this mixture at this temperature. 148.5 g (1.6 mol) of phosgene are then passed in, during which the temperature is kept at 0° C. by intensive cooling. When the reaction has ended, excess phosgene is removed under a water pump vacuum at 20° C. The residue which remains is dissolved in 350 ml of 1,2-dichloroethane, and 30 g (1.5 mol) of anhydrous hydrogen fluoride are added. The apparatus is sealed, a nitrogen pressure of 10 bar is applied and the mixture is heated to 120° C. It is stirred at this temperature for 20 hours. It is then allowed to cool, the excess hydrogen fluoride is removed under a water pump vacuum and the residue is poured onto ice. The mixture is rendered alkaline with solid potassium hydroxide and then extracted with methylene chloride. After the organic phase has been dried and concentrated, the residue is distilled.

38 g (68.5% of theory) of 2-fluoro-5-methylpyridine (boiling point$_{48-45}$=65°–75° C.) are obtained.

EXAMPLE 5

1st stage:

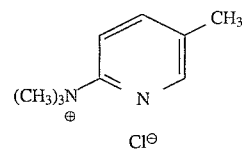

90 g (0.825 mol) of 3-methyl-pyridine 1-oxide are initially introduced into 540 ml of methylene chloride and the mixture is cooled to 0° C. 195 g (3.3 mol) of trimethylamine are condensed in at this temperature. 245 g (2.63 mol) of phosgene are then passed through the mixture, the temperature being held at 0° C. by intense cooling. After the end of the reaction, excess phosgene is removed at 20° C. under a water jet vacuum, The residue which remains is purified using column chromatography (silica gel; eluent: methylene chloride/methanol, vol. 10:1.5).

188 g of a product mixture which contains 102 g (66% of theory) of trimethyl-(5-methyl-pyridin-2-yl)-ammonium chloride, according to the $^1$H NMR spectrum are obtained.

NMR Data: $^1$H NMR (300 MHz, D$_6$-DMSO) δ/ppm=2.41 (3H, singlet); 3.64 (9H, Singlet); 8.06 (2H, AB-system, J$_{AB}$=8.4 Hz); 8.5 (1H, singlet)

2nd stage:

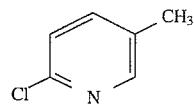

15 g of the product mixture from the first stage are heated to 100° C. A stream of phosgene is passed through the resulting melt for 6 hours at this temperature, the melt gradually becoming viscous. Finally excess phosgene is removed by means of a stream of nitrogen. The residue is then digested with 100 ml of methylene chloride, washed twice with water, dried with sodium sulphate and filtered. The solvent is carefully distilled off from the filtrate under a water jet vacuum.

2.43 g of a mixture of 2-chloro-5-methyl-pyridine and 2-chloro-3-methyl-pyridine in the ratio of 44;1 are obtained (according to analysis by gas chromatography). This corresponds to a yield of 28.3% of theory relative to the 3-methylpyridine 1-oxide used in the 1st stage. The unreacted intermediate of the formula (III) may be recovered by evaporating the combined aqueous phases. A yield of 2-chloro-5-methyl-pyridine of 90% of theory is calculated, relative to reacted intermediate.

EXAMPLE 6

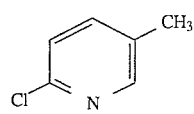

90 g (0.825 mol) of 3-methyl-pyridine 1-oxide are initially introduced into 540 ml of methylene chloride and the mixture is cooled to 0° C. At this temperature, 195 g (3.3 mol) of trimethylamine are condensed 245 g (2.63 mol) of phosgene are then passed through the mixture, the temperature being held at 0° C. by intense cooling. After the end of the reaction, the mixture is evaporated to dryness in a vacuum. The crude product which is obtained is heated to 100° C. and made stirrable by the addition of a small amount of acetonitrile. At this temperature, a stream of phosgene is passed through the mixture for 10 hours, the mixture gradually becoming viscous. Dilute sodium hydroxide solution is added with cooling, until the pH is 7–8. The mixture is extracted a total of 4 times with methylene chloride. The combined organic phases are dried with sodium sulphate and, after filtration, evaporated under a water jet vacuum.

28.8 g (27.4% of theory) of a mixture of 2-chloro-5-methylpyridine and 2-chloro-3-methylpyridine in the ratio of 47:1 are obtained (according to analysis by gas chromatography). Unreacted intermediate of the formula (III) may be recovered by evaporating the aqueous phase.

EXAMPLE 7

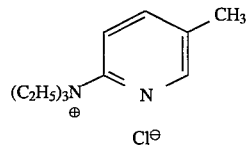

90 g (0.825 mol) of 3-methylpyridine 1-oxide are initially introduced into 540 ml of methylene chloride and the mixture is cooled to 0° C. 334 g (3.3 mol) of trimethylamine are condensed in at this temperature. 245 g (2.63 mol) of phosgene are then passed through the mixture, the temperature being held at 0° C. by intense cooling. After the end of the reaction, excess phosgene is removed at 20° C. under a water jet vacuum. The residue which remains is purified using column chromatography (silica gel; eluent: methylene chloride/methanol, vol. 10:1.5).

173 g of a product mixture Which contains, according to the $^1$N-NMR spectrum, 104 g (55% of theory) of triethyl (5-methyl-pyridin-2-yl)-ammonium chloride are obtained.

$^1$H-NMR (300 MHz, CDCl$_3$) δ/ppm=1.20 (9H, triplet, J=7.2 Hz), 2.44 (3H, singlet), 4.14 (6H, quartet, J=7.2 Hz), 7.98 (1H, multiplat, $J_{AB}$=8.4 Hz), 8.34 (1H, quartet, J=0.9 Hz), 8.63 (1H, doublet, $J_{AB}$= 8.7 Hz).

EXAMPLE 8

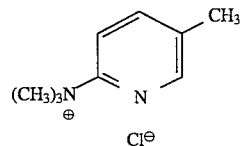

19.5 g (0.331 mol) of trimethylamine are condensed at −10° C. and added at −5° C. to a solution of 8.8 g (0.0807 mol) of 3-methyl-pyridine 1-oxide in 100 ml of methylene chloride. Then 6.9 ml (0.097 mol) of thionyl chloride in 10 ml of methylene chloride are added dropwise at the same temperature over a period of 30 minutes. During this addition the temperature is kept at below 0° C. The resulting yellow solution is allowed to thaw and is subsequently stirred overnight at room temperature.

A golden yellow solution is obtained, which is evaporated in a rotary evaporator at 20°–5° C. 24.5 g of a greasy solid is obtained which, according to $^1$H-NMR, contains about 14.5 g (96% of theory) of trimethyl-(5-methyl-pyridin-2-yl)-ammomium chloride.

$^1$H-NMR: (300 MHz, D$_6$-DMSO) δ/ppm=2.41 (3H, singlet); 3.64 (9H, singlet), 8.06 (2H, AB-System, $J_{AB}$=8.4 Hz), 8.5 (1H, singlet)

EXAMPLE 9

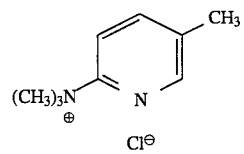

20.5 g (0.348 mol) of trimethylamine are condensed at −10° C. and then added at −5° C. to a solution of 8.8 g (0.0807 mol) of 3-methyl-pyridine 1-oxide in 110 ml of methylene chloride. Then a solution of 21.3 ml (0.2421 mol) of sulphuryl chloride in 20 ml of methylene chloride is added dropwise at the same temperature. A fine, white precipitate is formed which is thawed to room temperature over a period of one hour and is then stirred for a further 2 hours at this temperature. The precipitate dissolves completely during this time. The resulting golden yellow solution is left to stand overnight and is then evaporated in a rotary evaporator.

48.7 g of a greasy solid which, according to $^1$H-NMR, contains 11.6 g (77% of theory) of trimethyl-(5-methyl-pyridin-2-yl)-ammonium chloride, is obtained.

EXAMPLE 10

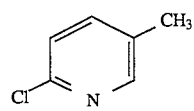

109 g (1.0 mol) of 3-methyl-pyridine 1-oxide are initially introduced into 800 ml of 1,2-dichloroethane and the mixture is cooled to −30° C. 130 g (2.2 mol) of trimethylamine are condensed in at this temperature and 212 g (1.2 mol) of benzene sulphochloride are then introduced over a period of 2 hours with continuous cooling. Then cooling is discontinued and the reaction mixture is stirred for 15 hours at 20° C. Then the mixture is heated to 35° C. and hydrogen chloride is introduced at this temperature until the reaction is complete according to analysis by thin-layer chromatography (duration: about 32 hours). The mixture is worked up by adjusting it to an alkaline pH value using a 20% sodium hydroxide solution and extracting the solution with dichloromethane. The organic phase is dried with sodium sulphate and filtered. The solvent is distilled off carefully from the filtrate under a water jet vacuum.

136 g of a crude product is obtained, which, according to analysis by gas chromatography, contains 78% of 2-chloro-5-methylpyridine.

Yield: 84% of theory,

It will be understood that the specification and examples are illustrative but not limitative of the present invention and that other embodiments within the spirit and scope of the invention will suggest themselves to those skilled in the art.

We claim:

1. A compound of the formula

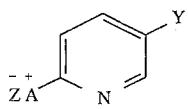

in which

A represents the cationic radical of an organic nitrogen base,

Z represents an anion formed on an electrophilic compound and

Y represents halogen, alkyl or halogenoalkyl.

2. A compound according to claim 1, wherein

A represents an organic nitrogen base selected from the group consisting of tri-($C_1$–$C_4$-alkyl)-amine, N,N-di($C_1$–$C_4$-alkyl)-benzylamine, N,N-di($C_1$–$C_4$-alkyl)-cyclohexylamine, and pyridine which is optionally mono- to trisubstituted by $C_1$–$C_4$-alkyl, Z represents a chloride ion or a $C_1$–$C_4$-alkyl-carboxylate ion; and Y represents fluorine, chlorine, bromine, iodine, or $C_1$–$C_4$-alkyl which is optionally mono- to trisubstituted by fluorine, chlorine or bromine.

3. A compound according to claim 1, wherein

A represents trimethylamine, triethylamine, tripropylamine tributylamine, N,N-dimethyl-benzyl-amine, N,N-diethylbenzylamine, N,N-dimethyl-cyclohexylamine, N,N-diethyl-cyclohexylamine or pyridine, which is optionally mono- or disubstituted by methyl or ethyl, Z represents a chloride ion or an acetate ion and Y represents fluorine, chlorine, bromine, ethyl, n- or i-propyl, n-, i-, s-, or t-butyl, trifluoromethyl, trichloromethyl, tribromomethyl, difluoromethyl, dichloromethyl, dibromomethyl, fluoromethyl, chloromethyl or bromomethyl.

4. A compound according to claim 1, wherein Y represents methyl.

* * * * *